(12) United States Patent
Steinhardt et al.

(10) Patent No.: US 8,906,090 B2
(45) Date of Patent: Dec. 9, 2014

(54) AUDITORY OSSICLE PROSTHESIS

(75) Inventors: Uwe Steinhardt, Hirrlingen (DE); Alex Huber, Kuesnacht (CH); Albrecht Eiber, Weinstadt (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 895 days.

(21) Appl. No.: 12/070,279

(22) Filed: Feb. 15, 2008

(65) Prior Publication Data

US 2008/0208338 A1 Aug. 28, 2008

(30) Foreign Application Priority Data

Feb. 23, 2007 (DE) .......................... 10 2007 008 851

(51) Int. Cl.
*A61F 2/18* (2006.01)

(52) U.S. Cl.
CPC ............. *A61F 2/18* (2013.01); *A61F 2002/183* (2013.01)
USPC .............................................. 623/10; 600/25

(58) Field of Classification Search
CPC .................................... A61F 2/18; A61F 2/183
USPC .................. 623/10, 16.11; 606/56, 57; 600/25
See application file for complete search history.

(56) References Cited

U.S. PATENT DOCUMENTS

| 3,469,573 | A | * | 9/1969 | Florio | 606/74 |
| 3,711,869 | A | | 1/1973 | Shea, Jr. | |
| 3,838,468 | A | * | 10/1974 | Armstrong | 623/10 |
| 4,655,776 | A | * | 4/1987 | Lesinski | 623/10 |
| 5,370,689 | A | | 12/1994 | Causse | |
| 5,935,167 | A | | 8/1999 | á Wengen | |
| 6,537,199 | B1 | | 3/2003 | Mueller et al. | |
| 6,554,861 | B2 | | 4/2003 | Knox et al. | |
| 6,830,587 | B2 | | 12/2004 | á Wengen et al. | |
| 7,628,812 | B2 | * | 12/2009 | aWengen et al. | 623/10 |
| 2001/0037151 | A1 | | 11/2001 | Knox et al. | |
| 2002/0045939 | A1 | * | 4/2002 | Kurz | 623/10 |
| 2007/0055372 | A1 | * | 3/2007 | Prescott et al. | 623/10 |

FOREIGN PATENT DOCUMENTS

| DE | 296 09 687 U1 | 10/1996 |
| DE | 202 12 771 U1 | 12/2002 |
| DE | 10 2004 038 078 A1 | 3/2006 |
| EP | 1 073 313 A2 | 1/2001 |
| EP | 0 809 982 B1 | 1/2003 |
| WO | WO 02/069850 A1 | 9/2002 |

OTHER PUBLICATIONS

German Patent Office Search Report dated Aug. 29, 2007.
European Search Report dated May 19, 2008.

* cited by examiner

*Primary Examiner* — Paul Prebilic
(74) *Attorney, Agent, or Firm* — Flynn, Thiel, Boutell & Tanis, P.C.

(57) ABSTRACT

An auditory ossicle prosthesis, which at one end has a first securing element for mechanical connection to a member of the ossicular chain, which securing element is designed in the form of a loop that encloses the member, is partially open to the outside via a slit-like aperture and engages with a force fit around the member, the slit-like aperture being considerably smaller than the diameter of the member engaged by the loop, wherein, after attachment, the loop bears with a force fit on the engaged member via at least three areas, and that, in the circumferential direction around the engaged member, at least three areas of the loop do not touch the engaged member but instead each extend at a distance from the surface of the latter.

14 Claims, 3 Drawing Sheets

AUDITORY OSSICLE PROSTHESIS

FIELD OF THE INVENTION

The invention relates to an auditory ossicle prosthesis which replaces or spans at least one member of the ossicular chain in humans, said auditory ossicle prosthesis having at least at one end a first securing element for mechanical connection to a member of the ossicular chain, in particular to the process of the anvil or to the manubrium of the hammer, which securing element is designed in the form of a loop that encloses the member, is partially open to the outside via a slit-like aperture and engages with a force fit around the member of the ossicular chain to which the mechanical connection is to be established, the slit-like aperture of the loop being considerably smaller than the diameter of the member engaged by the loop.

BACKGROUND OF THE INVENTION

An auditory ossicle prosthesis of this kind is, for example, known from German Utility Model DE 296 09 687 U1, from WO 02/069850 A1 or from U.S. Pat. No. 6,554,861 B2.

The role of the middle ear in humans, with its auditory ossicles, is to take up the sound waves impacting the tympanic membrane via the external acoustic meatus and transmit them to the fluid-filled inner ear. The three auditory ossicles are the hammer (malleus), which is attached to the tympanic membrane, the stirrup (stapes), which is connected via its footplate (basis stapedis) to the inner ear, and the anvil (incus), which is situated between the hammer and the stirrup and is connected to these in an articulated manner. In otosclerosis, a disease of the human petrous bone (the bone in which the whole ear sits), inflammatory-like processes affecting the bone may lead to a fixing of the normally loosely oscillating stirrup. As a result of this, the sound signal is not transmitted, or is transmitted only incompletely, to the inner ear via the ossicular chain, and this leads to impaired hearing.

Auditory ossicle prostheses are used to transmit sound from the tympanic membrane to the inner ear when the ossicles of the human middle ear are entirely or partially absent or damaged. The auditory ossicle prosthesis has two ends, and, depending on the individual circumstances of the patient, one end of the auditory ossicle prosthesis is fixed, for example, to the process of the anvil or to the manubrium of the hammer, and the other end is, for example, secured to the stirrup or plunged directly into the inner ear. With the known auditory ossicle prostheses, the sound conduction between the tympanic membrane and the inner ear is often made possible only to a limited extent, since these prostheses are able only to an extremely limited extent to replace the natural anatomical features of the ossicular chain.

An important problem when fitting an auditory ossicle prosthesis lies in the connection of the prosthesis to a member of the ossicular chain, since this connection should of course on the one hand be secure and permanent, but on the other hand should also be reasonably easy for the operator to establish. U.S. Pat. No. 3,711,869 A and U.S. Pat. No. 5,370,689 A, for example, have disclosed auditory ossicle prostheses that are secured on the process of the anvil by means of a slotted eyelet. However, special tools are needed to widen the eyelet and to make it easier to push the prosthesis onto the process of the anvil, and also to fix the prosthesis by pressing the slotted eyelet together, which proves quite awkward in practice.

An auditory ossicle prosthesis known from the above-mentioned German Utility Model DE 296 09 687 U1 of the Applicant is distinguished by being relatively easily to implant, by simply clipping it onto the long process of the anvil. It holds in place solely by the clamping action of the clip. No further securing means or special fixing methods are needed.

However, in the course of implantation, tilting of the prosthesis could occur, which would make the operation more difficult for the surgeon. To overcome this problem, in a "successor model" of this prosthesis, which is described in DE 202 12 771 U1, the clamp is lengthened with at least one of its legs protruding past the opening outward in the form of an arc, with which the prosthesis can be suspended, before being slipped on, from the long process of the anvil of the human middle ear, thus affording the surgeon the possibility of changing the surgical instruments and, for example, using a small hook to slip the prosthesis onto the long process of the anvil. In addition, this measure also allows the spring characteristic of the structure to be made considerable "softer". This results in considerably improved handling of the auditory ossicle prosthesis, because greater differences in the individual shape and size of the point of attachment on the auditory ossicle of the respective patient can also be easily compensated for, without having to keep different prostheses ready.

The known auditory ossicle prostheses according to the aforementioned WO 02/069850 A1 or U.S. Pat. No. 6,554,861 B2, which are made from a shape-memory metal, can also be fixed relatively easily at a desired site of an auditory ossicle with the aid of the first securing element likewise designed as a loop. By application of heat, the shape-memory metal, for example nitinol, is provided with the impulse to close. The prosthesis loop then "remembers" its original state and is in this way secured on the process of the anvil. Consequently, this appears to be an elegant alternative to the push-on clip, which is slightly more expensive to produce, according to DE 296 09 687 U1 or DE 202 12 771 U1.

However, the known loop prostheses of the kind described in WO 02/0698590 A1 or U.S. Pat. No. 6,554,861 B2 have the considerable disadvantage that they completely enclose the corresponding point of attachment on the auditory ossicle, generally the process of the anvil or the manubrium of the hammer, which in practice can often lead to strangulation of the mucosa lying on the surrounded bone area and, consequently, to necrosis of the structures lying behind this.

Although this problem is solved by an auditory ossicle prosthesis according to EP 0 809 982 B1 from the Applicant, said prosthesis is once again a prosthesis with a clip acting as the securing element.

By contrast, the object of the present invention is now to design the known loop prostheses using the simplest possible means, in such a way that many different geometries and external diameters of the individual points of attachment in the middle ear of the respective patient can be covered with a single auditory ossicle prosthesis, while nonetheless avoiding complete strangulation of the point of attachment on the auditory ossicle and ensuring that the vessels inside the mucosa of the bone are not damaged or that they can follow a new path after the auditory ossicle prosthesis has been secured.

With an auditory ossicle prosthesis of the type defined at the outset, this complex object is achieved, according to the invention, in a surprisingly simple but effective manner, by virtue of the fact that the loop is designed in such a way that, after attachment of the auditory ossicle prosthesis, it bears with a force fit on the engaged member via at least three inner areas, and that, in the circumferential direction around the engaged member, at least three inner areas of the loop, one of which can comprise the slit-like or slit-shaped aperture, do not touch the member engaged by the loop but instead each extend at a distance from the surface of the engaged member, and in which the inner areas bearing on the engaged member and the inner areas of the loop not touching the engaged member each alternate in the circumferential direction around the engaged member.

In this way, without major technical outlay and in a simple way, the advantages of the above-described known auditory ossicle prosthesis of WO 02/069850 A1 or of U.S. Pat. No. 6,554,861 B2, which define the generic type, can be made use of, while at the same time neatly avoiding their important disadvantages compared to the prostheses according to documents DE 296 09 687 U1, DE 202 12 771 U1 or EP 0 809 982 B1. As in the "push-on clip with gaps", which is slightly more complicated and expensive to produce, the modified loop of the first securing element of the auditory ossicle prosthesis according to the invention touches the supply vessels on the auditory ossicle only in the bearing areas. The other vessels run in the areas where the loop does not bear on the auditory ossicle, with the result that the supply of nutrients to the auditory ossicle, for example the long process of the anvil and the lenticular process, is not endangered.

A particularly preferred embodiment of the auditory ossicle prosthesis according to the invention is distinguished by the fact that the loop is constructed from flat band material and bears flat on the engaged member of the ossicular chain, as a result of which the pressure exerted locally by the securing element on the bone is distributed over a large surface area and in this way can be quite considerably reduced. In this way, it is possible to avoid the formation of constrictions and, therefore, the potential development of local necrosis.

Alternatively, however, the loop can also be constructed from wire material, which simplifies production, but can still entail the disadvantages described above.

These disadvantages can be avoided, or at least largely alleviated, in developments of this simple embodiment in which the wire material has a rectangular cross section, and the loop bears with a rectangle surface on the engaged member of the ossicular chain. In this way, as also in the case of the loop made from band material, the surface contact and the pressure exerted on the bone is distributed and locally reduced.

Embodiments of the invention are very particularly preferred in which the bearing points of the securing element on the auditory ossicle are distributed such as to ensure signal transmission free from distortion. This can be achieved by the fact that the areas via which the loop bears with a force fit on the engaged member of the ossicular chain are distributed symmetrically about the circumference of the engaged member.

In the auditory ossicle prosthesis according to the invention, the loop is generally arranged at one end of an elongate shaft that connects the loop to the other end of the auditory ossicle prosthesis, as is well known per se from the prior art.

In a geometrically particularly preferred development of this class of embodiments, an area via which the loop bears with a force fit on the engaged member of the ossicular chain is arranged in direct continuation of the shaft at the loop end of the latter. In this way, in the direction of the signal transmission through the auditory ossicle prosthesis, a force is introduced free of torque directly at the location of the mechanical attachment of the first securing element to the auditory ossicle.

In developments of the above embodiments, provision can alternatively or additionally be made that an area via which the loop bears with a force fit on the engaged member of the ossicular chain is arranged, in relation to the engaged member, lying diametrically opposite the direct continuation of the shaft at the loop end of the latter, as a result of which a favorable introduction of force during signal transmission is again achieved.

Other developments of the above-described class of embodiments are distinguished by the fact that an area that can comprise the slit-like aperture of the loop, and that does not touch the member of the ossicular chain engaged by the loop, is arranged in direct continuation of the shaft at the loop end of the latter.

After the prosthesis according to the invention has been placed surgically in the middle ear and the tympanic membrane has been closed again, the so-called incorporation phase starts. During this period, scars form and generate unpredictable forces, which can lead to the prosthesis shifting from its local position. For this reason, it is very useful if, after the operation, the prosthesis is able to compensate independently for a changed position in the middle ear. Since the anatomical features of the ear, for example the position, shape and size of the stirrup, anvil, hammer and tympanic membrane, also vary between individuals, it is generally very advantageous if auditory ossicle prostheses are not made rigid, but instead have a certain flexibility or variability. To achieve this flexibility or variability, various securing and coupling devices for auditory ossicles are known that have elastic parts and/or hinges. Such a hinged connection between a securing element, mounted on the footplate of the stirrup, and an elongate shaft of the auditory ossicle prosthesis is described per se in EP 1 181 907 B1 and is offered by the Applicant under the brand name "Ball-Joint-Prothese". In a particularly preferred embodiment of the auditory ossicle prosthesis according to the invention, at least one ball joint is therefore provided on or in the elongate shaft.

In addition to the post-operative change of position, a further problem also arises after implantation of auditory ossicle prostheses. This is due to the fact that the middle ear of the human body constitutes a "semi-open bearing". Any implantation material introduced into the body, in the context of a reconstruction of the middle ear and of its structures, is therefore subject to a particular stress arising from the fact that it lies in a contaminated and infected environment, which generally attacks the material. Since the aim of implanting an auditory ossicle prosthesis must be that the implant remains in the patient's middle ear for as long as possible and without complications, a protracted attack of the material can lead to damage of the prosthesis and/or to local infection. Both consequences are unacceptable. To prevent damage of the implanted material and also of the surrounding tissue on a permanent basis, another particularly preferred embodiment of the invention involves a biologically active coating, in particular a coating that inhibits growth and/or promotes growth and/or has an antibacterial action, being provided at least in some areas of the surface of the auditory ossicle prosthesis.

The auditory ossicle prosthesis according to the invention or parts thereof can be made of titanium and/or of tantalum and/or of steel and/or of an alloy of said metals. In addition to its strength and excellent sound conduction properties, the material titanium in particular is also known to have excellent biocompatibility in the middle ear in humans.

In view of the above-mentioned post-operative adjustment of position, embodiments of the invention are advantageous in which the prosthesis or parts thereof, in particular the loop, is made of a material with shape memory or with superelastic properties, preferably nitinol, which is known per se from, for example, the documents cited at the outset, namely WO 02/069850 A1 or U.S. Pat. No. 6,554,861 B2.

However, embodiments of the invention are also possible in which the prosthesis or parts thereof is/are made of biocompatible plastics, in particular silicone, polytetrafluoroethylene (PTFE) or composite fiber materials. Post-operative rejection reactions can also in most cases be avoided using these materials.

An embodiment of the device according to the invention is particularly preferred in which the weight distribution of the individual parts of the prosthesis is calculated as a function of a desired, predefinable frequency response of the sound conduction in the middle ear. It is thus possible, without major additional technical outlay, to achieve a degree of tuning of the sound propagation properties by means of an individually configured auditory ossicle prosthesis.

Such a tuning effect can be achieved, in particular embodiments, by the fact that at least one additional weight is secured on a part of the ossicular chain or of the prosthesis as a function of a desired, predefinable frequency response of the sound conduction in the middle ear.

In advantageous developments of these embodiments, the additional weight is secured on a part of the ossicular chain or the prosthesis by means of a clip. In addition, the additional weight and/or the clip can also be coated with a biologically active coating.

Depending on the individual defect that is to be remedied in a patient by use of the auditory ossicle prosthesis according to the invention, or that is at least to be alleviated in terms of its effects, the construction of the prosthesis is designed accordingly. In many embodiments, for example, the prosthesis can be secured at one end to the process of the anvil and at the other to the stirrup, or it can be plunged directly into the inner ear. In still further embodiments of the invention, the prosthesis is secured at one end to the manubrium of the hammer and at the other end to the anvil or to the stirrup, or is plunged directly into the inner ear. In this connection, an advantageous design is one in which the auditory ossicle prosthesis is located at the end point of the hammer (umbo) or directly next to it, as a result of which the maximum lever action is achieved for mechanically transmitting sound through movements in the artificial or natural ossicular chain. Other particularly preferred embodiments of the device according to the invention are distinguished by the fact that the auditory ossicle prosthesis is at one end coupled directly to the inner ear, in particular via a plunger, by means of perforation of the footplate of the stirrup (stapedectomy or stapedotomy) and/or by means of opening the human cochlea (cochleotomy).

In alternative embodiments of the auditory ossicle prosthesis according to the invention, the other end of the prosthesis remote from the loop can be provided with a second securing element, particularly also designed as a loop, as a closed bell, as a bell with one or more slits, or as a clip, for mechanical connection to a further member of the ossicular chain.

In further, particularly simple embodiments, the other end of the prosthesis remote from the loop is provided with a second securing element, designed in particular as a stamp or simple wire, for mechanical connection to the footplate of the stirrup without perforation.

A further embodiment of the invention, finally, is distinguished by the fact that the prosthesis is connected to an active vibration part of an active, in particular implantable hearing aid. In this way, further hearing damage can also be largely remedied by application of modern electronics or can at least be substantially alleviated in terms of its effects, in which case, on account of the above-described coating, a physical connection of the prosthesis to the outside world does not cause any problems resulting from increased bacterial ingress into the area of the middle ear, if the coating is made suitably antibacterial.

Further features and advantages of the invention will become clear from the following detailed description of illustrative embodiments of the invention, from the figures in the drawing, which shows important details of the invention, and also from the claims. The individual features can each be realized singly or in any desired combinations in variants of the invention.

BRIEF DESCRIPTION OF THE DRAWINGS

Illustrative embodiments of the invention are explained in more detail in the following description and are depicted in the schematic drawing, in which.

DETAILED DESCRIPTION

Figure 1:
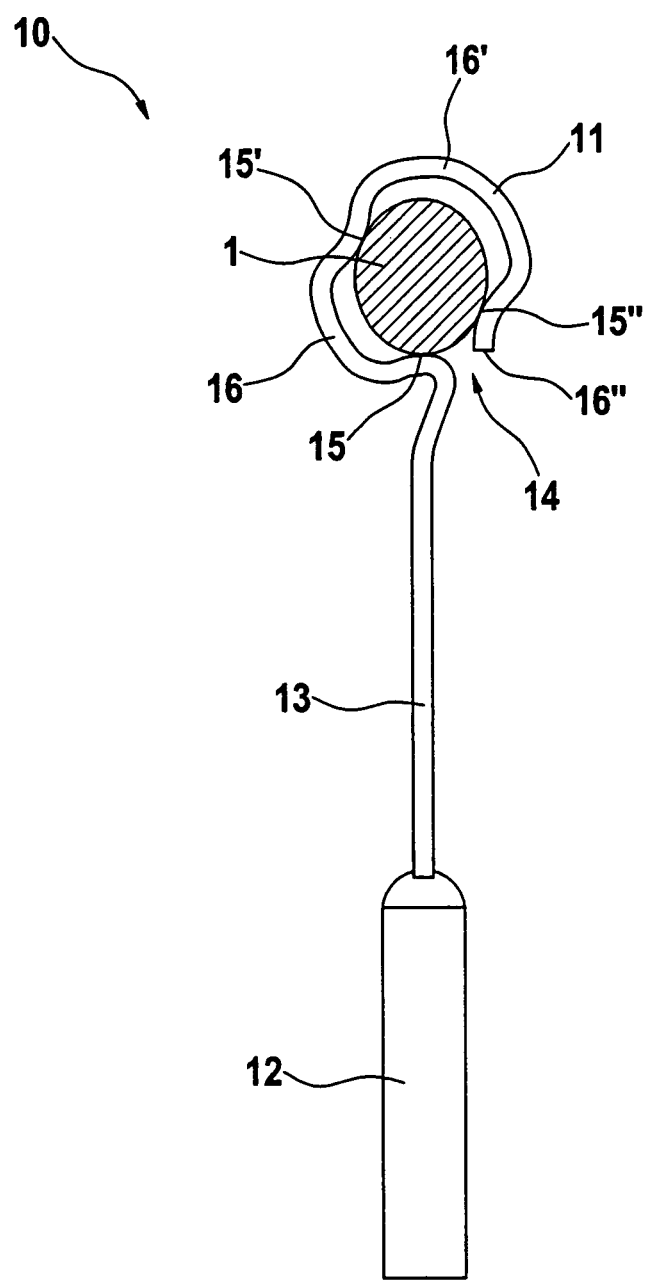
FIG. 1 shows a schematic view of a first embodiment of the auditory ossicle prosthesis according to the invention, with the loop bearing at three points on the ossicle, and with the loop bearing with a force fit on the elongate shaft.

In all the figures in the drawing, the engaged member of the ossicular chain is designated by reference number 1 and is shown schematically in cross section. In addition, all of the illustrated auditory ossicle prostheses 10; 20; 30 each have, at one of their ends, a first securing element in the form of a loop 11; 21; 31 and, at their opposite ends, a plunger 12; 22; 32. The loop 11; 21; 31 is in each case connected by an elongate shaft 13; 23; 33 to the plunger 12; 22; 32. As has been described above, other embodiments (not shown in the drawing) of the auditory ossicle prosthesis according to the invention can, at their end remote from the loop, have a securing element other than a plunger, for example another loop, a clip, a bell or the like.

FIG. 1 schematically shows an auditory ossicle prosthesis 10 in which the loop 11, after attachment of the prosthesis 10, bears with a form fit on the engaged member 1 via precisely three areas 15, 15', 15", and, in the circumferential direction around the enclosed member 1, a further three areas 16, 16, 16" of the loop 11, one of which comprises a slit-like or slit-shaped aperture 14, do not touch the member 1 engaged by the loop 11 but instead each extend at a distance from the surface of the engaged member 1. The punctiform bearing (or a small bearing surface) of the loop 11 in the three areas 15, 15', 15" ensures a secure connection. The first bearing point 15 lies at the 6 o'clock position relative to the shaft 13, the second bearing point 15' lies at the 10 o'clock position, and the third bearing point 15" lies at the 4 o'clock position. A particular advantage of this symmetrical arrangement is the introduction of force at the 6 o'clock position in the direction of the signal transmission, with no torque occurring. The loop 11 has a center area defined radially inwardly of, and in the same plane as the first three areas 15, 15', 15" that separately contact the surface of member 1 as shown in FIG. 1. Further, a longitudinal axis of the shaft 13 extends through the center area of the loop 11.

Figure 2:
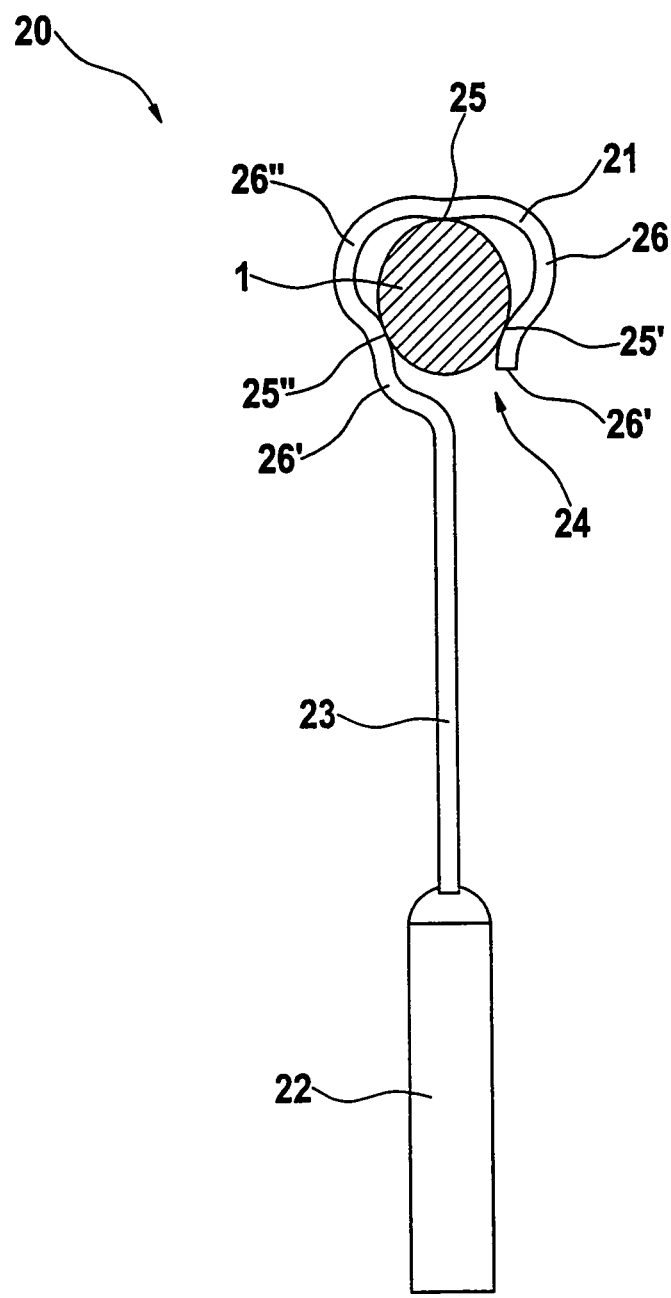
FIG. 2 shows another embodiment with the loop bearing at three points on the auditory ossicle, but not bearing with a force fit on the shaft.

The auditory ossicle prosthesis 20 shown in FIG. 2 also has a symmetrical three-point bearing at the three areas 25, 25', 25", while a further three areas 26, 26', 26" do not touch the ossicular chain member 1 engaged by the loop 21. Here, however, the area 26' comprising the slit-like aperture 24 of the loop 21 is arranged in direct continuation of the shaft 23 at the loop end thereof. As the loop 21 is a continuation of the shaft 23, a first end of the loop 21 is secured to or integral with the shaft 23 while the second open end of the loop 21 defines a side of the slit-shaped aperture shown in FIG. 2. Further, the bearing area 25 is disposed diametrically opposite the longitudinal axis of the shaft 23 at the first end of the shaft as shown in FIG. 2.

Figure 3:
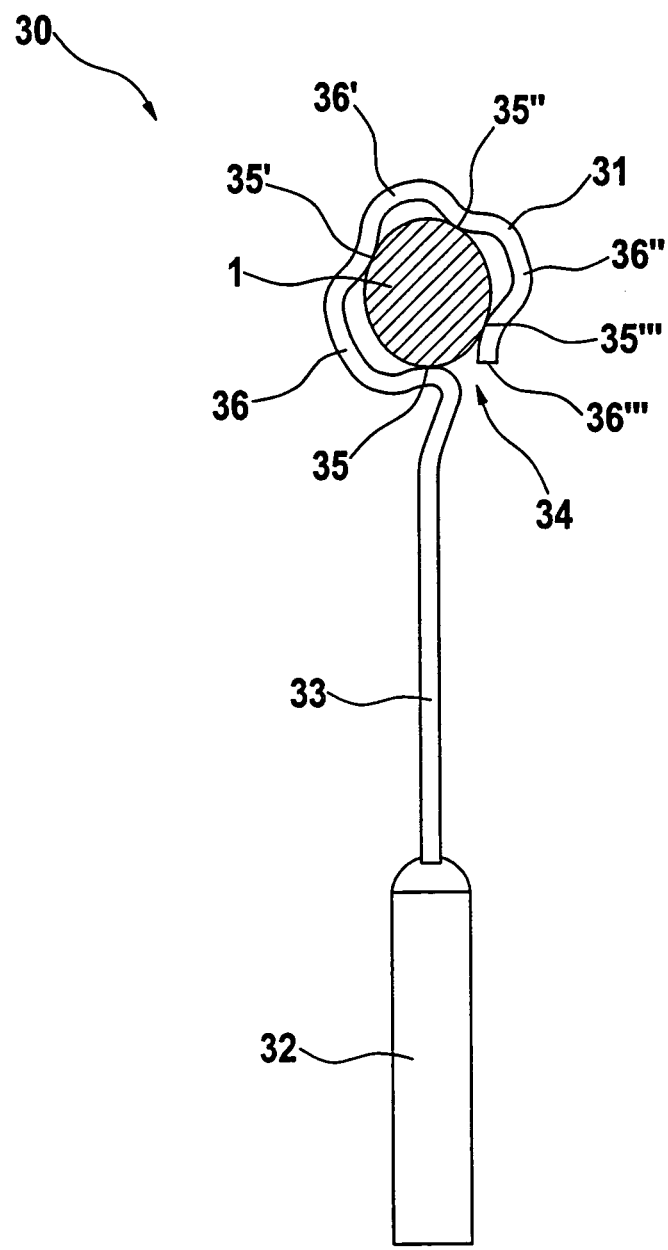
FIG. 3 shows a schematic view of a third embodiment, with the loop bearing at four points on the auditory ossicle, and also with the loop bearing with a force fit on the elongate shaft.

The prosthesis 30 in FIG. 3, finally, has a symmetrical four-point bearing at the four areas 35, 35', 35", 35''', while a further four separate areas 36, 36', 36", 36''' do not touch the ossicular chain member 1 engaged by the loop 31. The first bearing point of area 35 lies at the 6 o'clock position relative to the shaft 33, as in the embodiment according to FIG. 1, the second one lies at the 10 o'clock position, the third one at the 1 o'clock position, and the fourth one at the 4 o'clock position. The advantage of this embodiment is again that force is introduced free of torque at the 6 o'clock position in the direction of the signal transmission. At the 6 o'clock position shown in FIG. 3, the area or bearing point 35 that bears against the member is disposed along an extension of the longitudinal axis defined by the shaft 33. Moreover, this arrangement avoids an excessively large gap between the bearing points, which could lead to insufficient fixing of the prosthesis in the case of a small process of the anvil. Likewise, in FIG. 1, area 15 is located at the 6 o'clock position along an axis defined by the shaft 13.

The auditory ossicle prostheses according to the invention may differ in some respects, including their length and also the strength of the material used.

To achieve a certain hinge quality, some embodiments (also not shown in the drawing) can have a hinge area or a large number of hinge areas which act on one another and are generally arranged on or in the elongate shaft 13; 23; 33.

To additionally improve hearing quality, other embodiments not shown in the drawing can comprise a weight which is mounted on the elongate shaft 13; 23; 33 and serves for fine tuning of the acoustic properties of the auditory ossicle prosthesis by means of a targeted shifting of the resonance frequency to a desired value.

Moreover, the outer surface of the auditory ossicle prosthesis 10; 20; 30 can be provided with a biologically active coating which, depending on requirements, inhibits growth or promotes growth. A coating that inhibits growth is of particular importance especially in the area where the plunger 12; 22; 32 passes through the opening in the footplate of the stirrup, since here the prosthesis sits in the inner ear and is intended to oscillate, such that fusion at this point must be avoided in each case. The growth-inhibiting coating therefore acts here as a separating layer. The coating can also have microbicidal, in particular antibacterial actions and, after implantation of the prosthesis 10; 20; 30 in the middle ear, can independently release substances, in particular antibiotics, continuously into its environment over a long period of time.

What is claimed is:

1. An auditory ossicle prosthesis, comprising:
    an elongated shaft having a proximate end, a distal end, and a longitudinal axis; and
    a securing loop at the distal end of the shaft and having an outer diameter, the securing loop comprising a flat band material and having at least three inwardly projecting areas spaced apart from each other for providing flat bearing engagement with an oval-shaped member of an ossicular chain in a human ear by being disposed circumferentially around such an oval-shaped member, the securing loop having a central area radially inwardly of each of the three inwardly projecting areas, a first loop end secured to the distal end of the shaft, and a second loop end spaced from the shaft, one of the at least three inwardly projecting areas of the securing loop being disposed at the distal end of the elongated shaft and oriented to project inwardly and also being aligned with the longitudinal axis of the elongated shaft for contacting an oval-shaped member of an ossicular chain,
    the second loop end and the distal end of the shaft together defining a slit-shaped aperture, the size of which is adjustable during installation of the auditory ossicle prosthesis to provide a force fit about an oval-shaped member of an ossicular chain,
    the auditory ossicle prosthesis being shaped such that an extension of the longitudinal axis of the shaft crosses the central area of the securing loop.

2. The auditory ossicle prosthesis according to claim 1, wherein one of the three inwardly projecting areas of the securing loop lies at a twelve o'clock position relative to the shaft.

3. The auditory ossicle prosthesis according to claim 1, wherein the one inwardly projecting area of the securing loop disposed at the distal end of the elongated shaft is a direct continuation of the shaft.

4. The auditory ossicle prosthesis according to claim 1, wherein the securing loop is a wire material.

5. The auditory ossicle prosthesis according to claim 4, wherein the wire material has a rectangular cross section.

6. The auditory ossicle prosthesis according to claim 1, wherein the proximate end of the shaft defines an end of the auditory ossicle prosthesis.

7. The auditory ossicle prosthesis according to claim 1, wherein the auditory ossicle prosthesis includes a plunger at the proximate end of the shaft for coupling directly to an inner ear.

8. The auditory ossicle prosthesis according to claim 1, wherein the securing loop is of a shape-memory material.

9. The auditory ossicle prosthesis according to claim 1, wherein the auditory ossicle prosthesis comprises at least one material of the group consisting of titanium, steel, tantalum, and an alloy of one or more of these materials.

10. The auditory ossicle prosthesis according to claim 1, wherein the auditory ossicle prosthesis comprises a biocompatible plastic.

11. The auditory ossicle prosthesis according to claim 1, further comprising a biologically active coating which inhibits growth or promotes growth or has an antibacterial action.

12. The auditory ossicle prosthesis according to claim 1, wherein the weight distribution of the prosthesis is balanced as a function of a desired, predefinable frequency response of sound conduction in a middle ear.

13. The auditory ossicle prosthesis according to claim 8, wherein the shape-memory material is nitinol.

14. The auditory ossicle prosthesis of claim 10, wherein the biocompatible plastic comprises at least one material from the group consisting of silicone, polytetrafluoroethylene, and composite fiber materials.

* * * * *